US009911392B2

(12) United States Patent
Nitta et al.

(10) Patent No.: US 9,911,392 B2
(45) Date of Patent: Mar. 6, 2018

(54) MEDICAL IMAGE DIAGNOSIS APPARATUS AND IMAGE DISPLAY APPARATUS

(71) Applicant: TOSHIBA MEDICAL SYSTEMS CORPORATION, Otawara-shi, Tochigi (JP)

(72) Inventors: Shuhei Nitta, Tokyo (JP); Tomoyuki Takeguchi, Kanagawa (JP); Nobuyuki Matsumoto, Tokyo (JP); Masahiro Sekine, Tokyo (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 87 days.

(21) Appl. No.: 14/548,902

(22) Filed: Nov. 20, 2014

(65) Prior Publication Data
US 2015/0084959 A1    Mar. 26, 2015

Related U.S. Application Data

(63) Continuation of application No. PCT/JP2013/064268, filed on May 22, 2013.

(30) Foreign Application Priority Data

May 22, 2012 (JP) ................. 2012-116643

(51) Int. Cl.
*G06T 15/08* (2011.01)
*G09G 5/00* (2006.01)
(Continued)

(52) U.S. Cl.
CPC ............. *G09G 5/006* (2013.01); *A61B 5/055* (2013.01); *A61B 5/7425* (2013.01); *G06T 11/60* (2013.01);
(Continued)

(58) Field of Classification Search
CPC ....... G06T 2207/30048; G06T 2210/41; G06T 7/0012; G06T 2207/30004
See application file for complete search history.

(56) References Cited

U.S. PATENT DOCUMENTS 5,311,131 A * 5/1994 Smith .................... G01R 33/58
324/309
6,381,296 B1   4/2002 Nishiura
(Continued)

FOREIGN PATENT DOCUMENTS

JP    1-134580     5/1989
JP    2002-140689  5/2002
(Continued)

OTHER PUBLICATIONS

International Search Report for PCT/JP2013/064268 dated Jun. 25, 2013.
(Continued)

*Primary Examiner* — Barry Drennan
*Assistant Examiner* — Phong Nguyen
(74) *Attorney, Agent, or Firm* — Nixon & Vanderhye P.C.

(57) ABSTRACT

A medical image diagnosis apparatus according to an embodiment includes a controller. The controller generates a plurality of candidates for a first cross-sectional image from three-dimensional image data obtained by taking images of a heart. The controller generates, from the three-dimensional image data, one or more second cross-sectional images each of which intersects the candidates for the first cross-sectional image. The controller displays in parallel on a display, the candidates for the first cross-sectional image, as well as the second cross-sectional images on each of which information is superimposed. The information indi-
(Continued)

cates positional relationships between the candidates for the first cross-sectional image and the second cross-sectional image.

19 Claims, 11 Drawing Sheets

(51) Int. Cl.
*A61B 5/055* (2006.01)
*A61B 5/00* (2006.01)
*G06T 11/60* (2006.01)
*A61B 6/00* (2006.01)
*A61B 8/08* (2006.01)
*A61B 8/00* (2006.01)

(52) U.S. Cl.
CPC .............. *G06T 15/08* (2013.01); *A61B 6/463* (2013.01); *A61B 6/503* (2013.01); *A61B 8/0883* (2013.01); *A61B 8/463* (2013.01); *A61B 2576/023* (2013.01); *G06T 2210/41* (2013.01); *G09G 2340/14* (2013.01); *G09G 2380/08* (2013.01)

(56) References Cited

U.S. PATENT DOCUMENTS

| | | | | |
|---|---|---|---|---|
| 2004/0210138 | A1* | 10/2004 | Murashita | A61B 8/08 600/443 |
| 2008/0304730 | A1* | 12/2008 | Abe | A61B 8/08 382/131 |
| 2009/0010519 | A1* | 1/2009 | Wakai | G06F 19/321 382/131 |
| 2009/0015587 | A1* | 1/2009 | Hashimoto | A61B 8/06 345/424 |
| 2009/0060306 | A1* | 3/2009 | Ohuchi | A61B 8/0858 382/131 |
| 2009/0060309 | A1* | 3/2009 | Tsujii et al. | G06T 15/08 382/131 |
| 2009/0103794 | A1* | 4/2009 | Sathyanarayana | G06T 7/0012 382/131 |
| 2009/0129656 | A1* | 5/2009 | Filatov | G06T 7/0012 382/132 |
| 2009/0270732 | A1* | 10/2009 | Abe | A61B 8/0883 600/443 |
| 2010/0195887 | A1* | 8/2010 | Abe | A61B 8/08 382/131 |
| 2011/0178405 | A1* | 7/2011 | Chono | A61B 8/0883 600/443 |
| 2011/0282207 | A1 | 11/2011 | Hashimoto | |
| 2011/0301462 | A1* | 12/2011 | Hashimoto | A61B 8/0883 600/443 |
| 2011/0313291 | A1* | 12/2011 | Chono | A61B 8/08 600/440 |
| 2012/0027276 | A1* | 2/2012 | Chono | A61B 5/02028 382/128 |
| 2012/0134566 | A1 | 5/2012 | Nitta et al. | |
| 2012/0316441 | A1* | 12/2012 | Toma | A61B 8/4245 600/441 |
| 2014/0219534 | A1* | 8/2014 | Wiemker | G06T 7/0012 382/131 |

FOREIGN PATENT DOCUMENTS

| | | |
|---|---|---|
| JP | 2003-325513 | 11/2003 |
| JP | 4018303 | 9/2007 |
| JP | 2009-78122 A | 4/2009 |
| JP | 2009-112374 A | 5/2009 |
| JP | 2009-279218 A | 12/2009 |
| JP | 2011-239890 | 12/2011 |
| WO | 2010/092918 A1 | 8/2010 |
| WO | WO 2011/021254 | 2/2011 |

OTHER PUBLICATIONS

Written Opinion of the International Searching Authority dated Jun. 25, 25, 2013.
Office Action dated Jan. 29, 2016 in CN 201380019573.2.
Japanese office action dated May 23, 2017 in Patent Application No. JP 2013-108359.

* cited by examiner

MEDICAL IMAGE DIAGNOSIS APPARATUS AND IMAGE DISPLAY APPARATUS

CROSS-REFERENCE TO RELATED APPLICATIONS

This application is a continuation of International Application No. PCT/JP2013/064268, filed on May 22, 2013 which claims the benefit of priority of the prior Japanese Patent Application No. 2012-116643, filed on May 22, 2012, the entire contents of which are incorporated herein by reference.

FIELD

Embodiments disclosed herein relate generally to a medical image diagnosis apparatus and an image display apparatus.

BACKGROUND

Conventionally, medical image diagnosis apparatuses such as Magnetic Resonance Imaging (MRI) apparatuses, X-ray Computed Tomography (CT) apparatuses, and ultrasound diagnosis apparatuses are configured to acquire three-dimensional image data (hereinafter, "volume data") of a target site and to generate a desired cross-sectional image from the acquired volume data. A cross-sectional image called a "basic cross-sectional image", for example, is useful for performing a diagnosis process on a desired site, when being displayed on a medical image diagnosis apparatus or an image display apparatus. In contrast, a cross-sectional image that intersects the "basic cross-sectional image" is called an "auxiliary cross-sectional image", for example, and is used for checking to see if the "basic cross-sectional image" is properly set or not.

For example, an MRI apparatus is configured to generate a basic cross-sectional image and an auxiliary cross-sectional image from volume data obtained by taking images of the heart and to display the basic cross-sectional image and the auxiliary cross-sectional image arranged in a row on the display. In that situation, an operator of the MRI apparatus repeatedly corrects and checks the basic cross-sectional image, while viewing the cross-sectional images displayed on the display.

DETAILED DESCRIPTION

A medical image diagnosis apparatus according to an embodiment includes a controller. The controller generates a plurality of candidates for a first cross-sectional image from three-dimensional image data obtained by taking images of a heart. The controller generates, from the three-dimensional image data, one or more second cross-sectional images each of which intersects the candidates for the first cross-sectional image. The controller displays in parallel on a display, the candidates for the first cross-sectional image, as well as the second cross-sectional images on each of which information is superimposed. The information indicates positional relationships between the candidates for the first cross-sectional image and the second cross-sectional image.

In the following sections, exemplary embodiments of a medical image diagnosis apparatus and an image display apparatus will be explained. In the exemplary embodiments, the medical image diagnosis apparatus is assumed to be an MRI apparatus.

Figure 1:
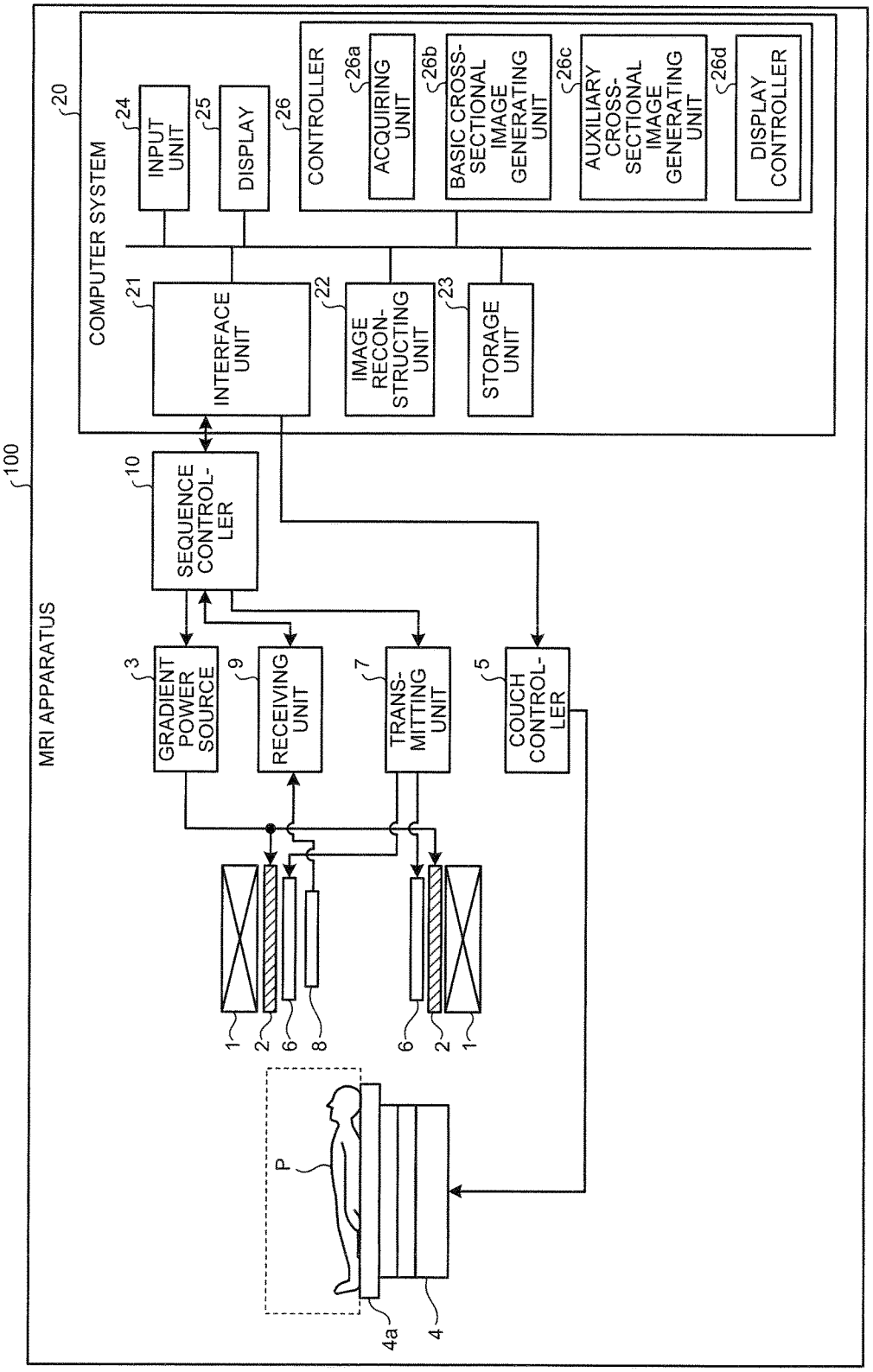
FIG. 1 is a block diagram of an MRI apparatus according to an embodiment.

FIG. 1 is a block diagram of an MRI apparatus 100 according to an embodiment. The MRI apparatus 100 does not include an examined subject (hereinafter, a "patient") P (shown in a dotted-line frame in FIG. 1). A magnetostatic field magnet 1 is formed in the shape of a hollow circular cylinder and is configured to generate a uniform magnetostatic field in the space on the inside thereof. The magnetostatic field magnet 1 may be configured by using, for example, a permanent magnet or a superconductive magnet. A gradient coil 2 is formed in the shape of a hollow circular cylinder and is configured to generate a gradient magnetic field in the space on the inside thereof. More specifically, the gradient coil 2 is disposed on the inside of the magnetostatic field magnet 1 and generates the gradient magnetic field by receiving a supply of a gradient pulse from a gradient power source 3. According to a control signal transmitted from a sequence controller 10, the gradient power source 3 is configured to supply the gradient pulse to the gradient coil 2.

A couch 4 includes a couchtop 4a on which the patient P is placed. While the patient P is placed thereon, the couchtop 4a is inserted into the hollow, which is an image taking opening, of the gradient coil 2. Normally, the couch 4 is provided so that the longitudinal direction thereof extends parallel to the central axis of the magnetostatic field magnet 1. A couch controller 5 is configured to drive the couch 4 so that the couchtop 4a moves in the longitudinal direction and in an up-and-down direction.

A transmission coil 6 is configured to generate a magnetic field. More specifically, the transmission coil 6 is disposed on the inside of the gradient coil 2 and generates the magnetic field by receiving a supply of a Radio Frequency (RF) pulse from a transmitting unit 7. According to a control signal transmitted from the sequence controller 10, the transmitting unit 7 is configured to supply the RF pulse corresponding to a Larmor frequency to the transmission coil 6.

A reception coil 8 is configured to receive magnetic resonance signals (hereinafter, "MR signals"). More specifically, the reception coil 8 is disposed on the inside of the gradient coil 2 and receives the MR signals emitted from the patient P due to an influence of the magnetic field. Further, the reception coil 8 outputs the received MR signals to a receiving unit 9.

According to a control signal transmitted from the sequence controller 10, the receiving unit 9 is configured to generate MR signal data on the basis of the MR signals being output from the reception coil 8. More specifically, the receiving unit 9 generates the MR signal data by applying a digital conversion to the MR signals being output from the reception coil 8 and further transmits the generated MR signal data to a computer system 20 via the sequence controller 10. The receiving unit 9 may be provided on a gantry device side where the magnetostatic field magnet 1, the gradient coil 2, and like are provided.

The sequence controller 10 is configured to control the gradient power source 3, the transmitting unit 7, and the receiving unit 9. More specifically, the sequence controller 10 transmits the control signals based on pulse sequence execution data transmitted from the computer system 20, to the gradient power source 3, to the transmitting unit 7, and to the receiving unit 9. For example, the sequence controller 10 is configured by using an integrated circuit such as an Application Specific Integrated Circuit (ASIC) or a Field Programmable Gate Array (FPGA), or an electronic circuit such as a Central Processing Unit (CPU) or a Micro Processing Unit (MPU).

The computer system 20 includes an interface unit 21, an image reconstructing unit 22, a storage unit 23, an input unit 24, a display 25, and a controller 26. The interface unit 21 is connected to the sequence controller 10 and is configured to control inputs and outputs of data that is transmitted and received between the sequence controller 10 and the computer system 20. The image reconstructing unit 22 is configured to reconstruct image data from the MR signal data transmitted from the sequence controller 10 and to store the reconstructed image data into the storage unit 23.

The storage unit 23 stores therein the image data stored therein by the image reconstructing unit 22 and other data used by the MRI apparatus 100. For example, the storage unit 23 is configured by using a semiconductor memory element such as a Random Access Memory (RAM) or a flash memory, or a hard disk, an optical disk, or the like.

The input unit 24 is configured to receive various types of instructions from an operator. For example, the input unit 24 is a user interface such as a mouse, a keyboard, a trackball, a touchpad, and/or the like. The display 25 is configured to display image data and the like. The display 25 is configured by using, for example, a liquid crystal display device or the like.

The controller 26 is configured to comprehensively control the MRI apparatus 100, by controlling the functional units described above. For example, the controller 26 is configured by using an integrated circuit such as an ASIC or an FPGA, or an electronic circuit such as a CPU or an MPU as digital signal processing circuitry driving a display screen.

In the present example, the controller 26 according to the present embodiment includes, as illustrated in FIG. 1, an acquiring unit 26a, a basic cross-sectional image generating unit 26b, an auxiliary cross-sectional image generating unit 26c, and a display controller 26d. Further, the controller 26 is configured to acquire volume data of the heart of the patient P, to generate candidates for a basic cross-sectional image and auxiliary cross-sectional images from the acquired volume data, and to display the generated cross-sectional images on the display 25.

First, the acquiring unit 26a acquires volume data of a region that encloses therein the heart of the patient P and outputs the acquired volume data to the basic cross-sectional image generating unit 26b and to the auxiliary cross-sectional image generating unit 26c. For example, the acquiring unit 26a generates the pulse sequence execution data for controlling the gradient power source 3, the transmitting unit 7, and the receiving unit 9 and further transmits the generated pulse sequence execution data to the sequence controller 10.

Further, from the volume data acquired by the acquiring unit 26a, the basic cross-sectional image generating unit 26b generates a plurality of candidates for a basic cross-sectional image and outputs the generated candidates for the basic cross-sectional image to the display controller 26d. For example, from the volume data acquired by the acquiring unit 26a, the basic cross-sectional image generating unit 26b calculates positions of the candidates for the basic cross-sectional image and generates the candidates from the volume data according to the calculated positions of the candidates.

Further, from the volume data acquired by the acquiring unit 26a, the auxiliary cross-sectional image generating unit 26c generates auxiliary cross-sectional images each of which intersects the candidates for the basic cross-sectional image and further outputs the generated auxiliary cross-sectional images to the display controller 26d. For example, from the volume data acquired by the acquiring unit 26a, the auxiliary cross-sectional image generating unit 26c calculates positions of the auxiliary cross-sectional images and generates the auxiliary cross-sectional images from the volume data according to the calculated positions of the auxiliary cross-sectional images.

Further, on the display 25, the display controller 26d displays the candidates for the basic cross-sectional image and the auxiliary cross-sectional images that are arranged in a matrix formation. For example, the display controller 26d displays the candidates for the basic cross-sectional image that are arranged in a row in either a horizontal direction or a vertical direction and displays the auxiliary cross-sectional images that are arranged in a row in either the vertical direction or the horizontal direction that is different from the direction in which the candidates are arranged. In this situation, in each of the auxiliary cross-sectional images, the display controller 26d displays information indicating positional relationships with the candidates for the basic cross-sectional image, in a superimposed manner.

Figure 2A:
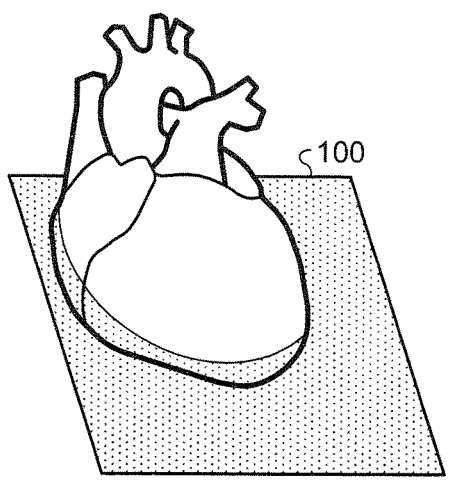
FIG. 2A-2B are drawings for explaining candidates for a basic cross-sectional image according to the present embodiment.
Figure 2B:
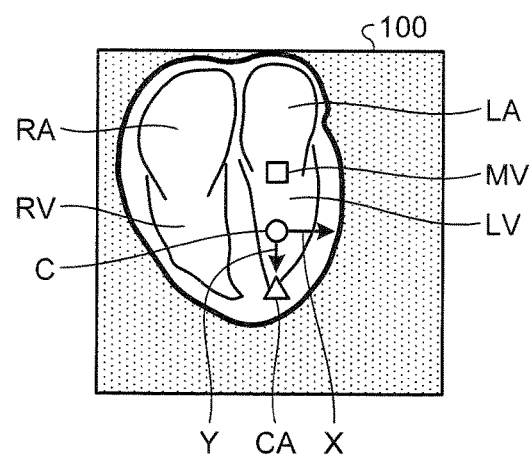

FIG. 2A-2B are drawings for explaining the candidates for the basic cross-sectional image according to the present embodiment. In the present embodiment, the basic cross-sectional image is assumed to be a "four-chamber view"; however, possible embodiments are not limited to this example. As for the heart, the basic cross-sectional image thereof may be any long-axis view of the heart, such as a vertical long-axis view, a horizontal long-axis view, a two-chamber view, or a three-chamber view.

FIG. 2A illustrates an anatomical positioning of a four-chamber view 100. FIG. 2B illustrates an example of the four-chamber view 100. As shown in FIG. 2B, the four-chamber view 100 is a cross-sectional image in which all of the four chambers (i.e., the left ventricle (LV), the left atrium (LA), the right ventricle (RV), and the right atrium (RA)) are visible and that crosses the mitral valve (MV) and the cardiac apex (CA), which are characteristic sites of the heart. In FIG. 2B, "C" denotes a site called "the center of the left ventricle" and is positioned at the middle point between the mitral valve MV and the cardiac apex CA. A vector from the center C of the left ventricle to the cardiac apex CA will be referred to as a "long axis Y", whereas a vector that is orthogonal to the long axis Y in the four-chamber view 100 will be referred to as a "short axis X". In the present embodiment, the basic cross-sectional image generating unit 26b generates a first candidate for the basic cross-sectional image that is a cross-sectional image containing the long axis Y of the heart and a second candidate for the basic cross-sectional image that is a cross-sectional image obtained by rotating the first candidate by a predetermined angle while the long axis Y is used as the rotation axis. In other words, the candidates for the basic cross-sectional image are cross-sectional images obtained by rotating the four-chamber view 100 shown in FIG. 2 by the predetermined mutually-different rotation angles, while the long axis Y is used as the rotation axis.

Next, FIG. 3A-3D are drawings for explaining the auxiliary cross-sectional images according to the present embodiment. In the present embodiment, the auxiliary cross-sectional images are assumed to be "left ventricular short-axis views" each of which intersects the long axis Y; however, possible embodiments are not limited to this example. Each of the auxiliary cross-sectional images may be any cross-sectional image that intersects the basic cross-sectional image.

Figure 3A:
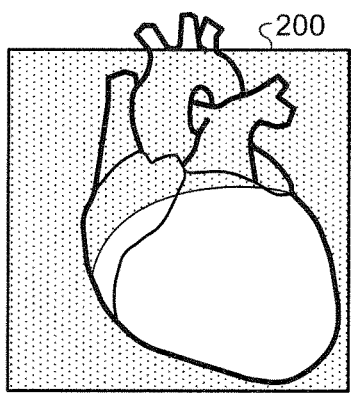
FIG. 3A-3D are drawings for explaining auxiliary cross-sectional images according to the present embodiment.
Figure 3B:
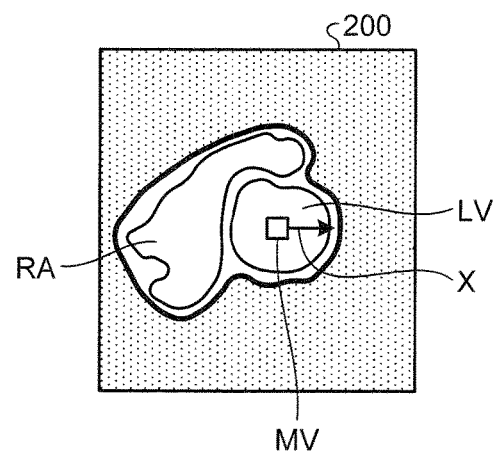
Figure 3C:
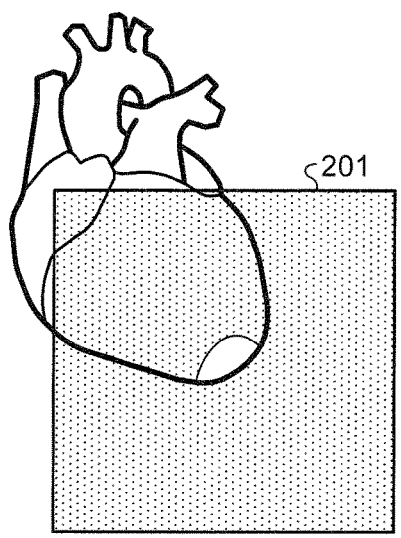
Figure 3D:
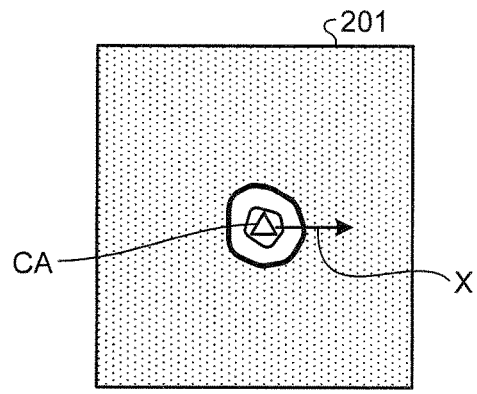

FIGS. 3A and 3C illustrate an anatomical positioning of left ventricular short-axis views 200 and 201, respectively. FIGS. 3B and 3D illustrate examples of the left ventricular short-axis views 200 and 201, respectively. As understood from FIGS. 2 and 3, each of the left ventricular short-axis views is a cross-sectional image orthogonal to the long axis Y. It is effective, like in the present embodiment, to obtain cross-sectional images that are orthogonal to the long axis Y at the positions corresponding to the mitral valve MR and the cardiac apex CA.

Figure 4:
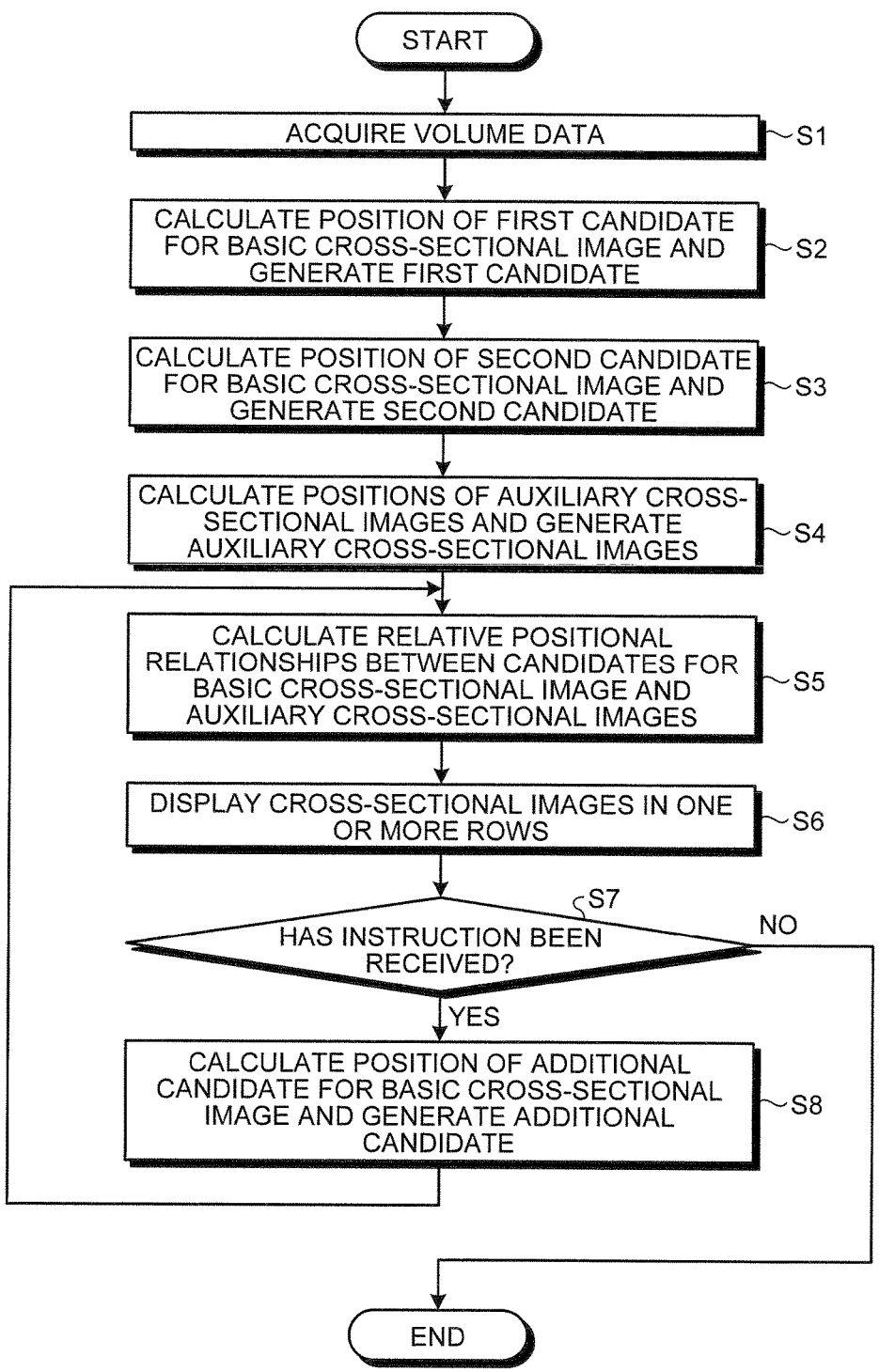
FIG. 4 is a flowchart of a processing procedure according to the present embodiment.

FIG. 4 is a flowchart of a processing procedure according to the present embodiment. In the present embodiment, it is assumed that the basic cross-sectional image generating unit 26b in advance receives, as an input from the operator via the input unit 24, the quantity of candidates for the basic cross-sectional image and an angle by which any of the candidates is rotated while the long axis of the heart is used as the rotation axis and that the received pieces of information are stored as parameters in a storage unit (not shown). After that, the basic cross-sectional image generating unit 26b generates the candidates for the basic cross-sectional image according to the parameters. Further, it is also assumed that, similarly, the auxiliary cross-sectional image generating unit 26c in advance receives, as an input from the operator via the input unit 24, the quantity of auxiliary cross-sectional images and positions of the auxiliary cross-sectional images and that the received pieces of information are stored as parameters in a storage unit (not shown). After that, the auxiliary cross-sectional image generating unit 26c generates the auxiliary cross-sectional images according to the parameters. When having received from the operator an instruction to change any of the parameters, the basic cross-sectional image generating unit 26b and the auxiliary cross-sectional image generating unit 26c may change the cross-sectional images to be generated according to the specifics of the instruction. Further, the parameters may be configured into the MRI apparatus 100 in advance, instead of being received as an input from the operator.

First, the acquiring unit 26a performs an image taking process while using the heart of the patient P as a target site and acquires volume data of the heart (step S1).

Subsequently, the basic cross-sectional image generating unit 26b calculates the position of a first candidate for the basic cross-sectional image from the volume data acquired at step S1 and generates the first candidate for the basic cross-sectional image from the volume data according to the calculated position of the first candidate (step S2).

Next, the calculation of the positions of the candidates for the basic cross-sectional image will be explained. More specifically, the basic cross-sectional image generating unit 26b sets the candidates for the basic cross-sectional image in a three-dimensional image space of the volume data in such a manner that at least the long axis Y is contained in the basic cross-sectional image. The positions of the candidates denote spatial positions of the candidates for the basic cross-sectional image in the three-dimensional image space. Each of the positions is expressed by a parameter (hereinafter, a "position parameter") that uniquely identifies a candidate for the basic cross-sectional image from the volume data.

For example, the position parameters can be expressed by using a coordinate point "o" of the center of a candidate for the basic cross-sectional image, the coordinate point "o" being expressed by Expression (1) below, as well as two vectors u and v that are orthogonal to each other and are positioned in the candidate for the basic cross-sectional image, the vectors u and v being expressed by Expression (2) below.

$$o = (o_x, o_y, o_z) \tag{1}$$

$$\left.\begin{array}{l} u = (u_x, u_y, u_z) \\ v = (v_x, v_y, v_z) \end{array}\right\} \tag{2}$$

The two vectors u and v are able to uniquely identify the position of each of the candidates for the basic cross-sectional image, unless the two vectors extend parallel to each other. In the present embodiment, for the sake of convenience in the explanation, the vectors u and v are assumed to be two vectors that are orthogonal to each other, while the vector u represents the short axis X, whereas the vector v represents the long axis Y. The coordinate point "o" represents the center C of the left ventricle. In other words, calculating the positions of the candidates for the basic cross-sectional image is to calculate the position parameters o, u, and v. The calculation of the positions of the candidates for the basic cross-sectional image can be realized by using a publicly-known technique. For example, the basic cross-sectional image generating unit 26b may prepare a template image of the basic cross-sectional image, in advance, so as to identify the center C of the left ventricle, the short axis X, and the long axis Y by performing a template matching process with the template image, and to calculate the position parameters expressing C, X, and Y. In another example, the basic cross-sectional image generating unit 26b may use a classifier capable of discriminating the basic cross-sectional image, so as to identify the center C of the left ventricle, the short axis X, and the long axis Y and to calculate the position parameters expressing C, X, and Y. In yet another example, the position parameters may be set manually.

In this situation, the position parameters do not necessarily have to be expressed by using the method described above. For example, the position parameters may be expressed as positions of the mitral valve MT and the cardiac apex CA and the short-axis vector u. It is acceptable to use any expressing method as long as, at least, it is possible to uniquely identify the position of each of the candidates for the basic cross-sectional image, and the information about the long axis Y is contained.

Subsequently, the basic cross-sectional image generating unit 26b calculates the position of a second candidate for the basic cross-sectional image from the volume data and generates the second candidate for the basic cross-sectional image from the volume data according to the calculated position of the second candidate (step S3).

The second candidate for the basic cross-sectional image is a cross-sectional image that is obtained in an auxiliary manner for the purpose of checking a cross-sectional image resulting from shifting the short axis X by a predetermined angle and is obtained by rotating the first candidate for the basic cross-sectional image by a predetermined angle while the long axis Y is used as the rotation axis.

In the present embodiment, the second candidate for the basic cross-sectional image can be expressed by using a coordinate point "$o_1$" of the center, the coordinate point "$o_1$" being expressed by Expression (3) below, as well as two vectors $u_1$ and $v_1$ that are orthogonal to each other and are positioned in the auxiliary cross-sectional image, the vectors $u_1$ and $v_1$ being expressed by Expression (4) below. In Expression (4), "θ" denotes the predetermined rotation angle by which the first candidate for the basic cross-sectional image is rotated while the long axis Y is used as the rotation axis, whereas "×" denotes calculating a cross product.

$$o_1 = o \qquad (3)$$

$$\left.\begin{matrix} u_1 = u\cos\theta + (1 - \cos\theta)(u \cdot v)v + v \times u\sin\theta \\ v_1 = v \end{matrix}\right\} \qquad (4)$$

After that, the auxiliary cross-sectional image generating unit 26c calculates, from the volume data, positions of the auxiliary cross-sectional images each of which is a cross section that intersects the candidates for the basic cross-sectional image and further generates the auxiliary cross-sectional images from the volume data according to the calculated positions of the auxiliary cross-sectional images (step S4).

Each of the auxiliary cross-sectional images is a cross-sectional image that is obtained in an auxiliary manner for the purpose of making it easier to recognize the positions of the candidates for the basic cross-sectional image and the long axis Y and is a cross-sectional image that intersects the long axis Y. For example, two or more auxiliary cross-sectional images are generated.

In the present embodiment, a left ventricular short-axis view serving as an auxiliary cross-sectional image can be expressed by using a coordinate point "$o_2$" of the center, the coordinate point "$o_2$" being expressed by Expression (5) below, as well as two vectors $u_2$ and $v_2$ that are orthogonal to each other and are positioned in the auxiliary cross section, the vectors $u_2$ and $v_2$ being expressed by Expression (6) below. In Expressions (5) and (6), "a" denotes an arbitrary constant, whereas "×" denotes calculating a cross product.

$$o_2 = o + av \qquad (5)$$

$$\left.\begin{matrix} u_2 = u \\ v_2 = u \times v \end{matrix}\right\} \qquad (6)$$

In the present embodiment, as shown in FIG. 3, the auxiliary cross-sectional image generating unit 26c sets two a's, so that the auxiliary cross-sectional images each correspond to the position of the mitral valve MV and to the position of the cardiac apex CA. By using the cross-sectional images that are orthogonal to the long axis Y as the auxiliary cross-sectional images like in the present embodiment, it is possible to recognize the positions of the candidates for the basic cross-sectional image and the position of the long axis Y more effectively. Further, it is even more effective if the cross-section position $o_2$ is set so as to correspond to the mitral valve MV and to the cardiac apex CA.

Subsequently, the display controller 26d calculates relative positional relationships between the candidates for the basic cross-sectional image and the auxiliary cross-sectional images (step S5). For example, the display controller 26d calculates intersecting line information between the first candidate for the basic cross-sectional image and the auxiliary cross-sectional images, intersecting line information between the second candidate for the basic cross-sectional image and the auxiliary cross-sectional images, and intersection point information between the auxiliary cross-sectional images and the long axis.

Figure 5:
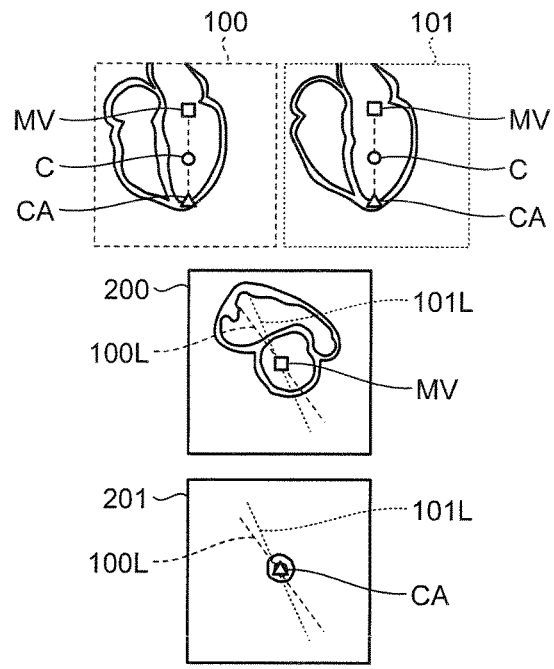
FIG. 5 is a drawing of an exemplary display according to the present embodiment.

FIG. 5 is a drawing of an exemplary display according to the present embodiment. An example of the calculation of the positional relationships will be explained, with reference to FIG. 5. In the present embodiment, the intersecting line information calculated by the display controller 26d corresponds to lines 100L and 101L shown in FIG. 5. The line 100L is an intersecting line with the first candidate 100 for the basic cross-sectional image, in each of the auxiliary cross-sectional images 200 and 201, and indicates the orientation of the short axis X. The line 101L is an intersecting line with a second candidate 101 for the basic cross-sectional image, in each of the auxiliary cross-sectional images 200 and 201, and indicates the orientation obtained by rotating the short axis X in the first candidate 100 by a predetermined angle, while the long axis Y is used as the rotation axis.

Generally speaking, an intersecting line vector 1 between each of the candidates for the basic cross-sectional image and an auxiliary cross-sectional image can be expressed by using Expression (7) shown below that uses a normal vector n of each of the candidates for the basic cross-sectional image and a normal vector n' of the auxiliary cross-sectional image. By projecting the vector 1 onto the auxiliary cross-sectional image, it is possible to calculate the intersecting line information with each of the candidates for the basic cross-sectional image in each of the auxiliary cross-sectional images 200 and 201. In expression (7), "b" is an arbitrary constant, whereas "p" is an arbitrary point on a line at which each of the candidates for the basic cross-sectional image intersects the auxiliary cross-sectional image, and it is possible to calculate "p" by solving an equation of the planes of the candidates for the basic cross-sectional image and the auxiliary cross-sectional image.

$$l = p + b(n \times n') \qquad (7)$$

Further, generally speaking, an intersection point (x, y, and z) between the long axis Y and an auxiliary cross-sectional image within a three-dimensional image space can be obtained by using Expression (10) shown below, where the equation of the plane of the auxiliary cross-sectional image 200 or 201 is defined by Expression (8), whereas the equation of the line l is defined by Expression (9). In the expressions below, "t" is a parametric variable. By projecting the intersection point within the three-dimensional image space that is obtained from Expression (10) onto the auxiliary cross-sectional image 200 or 201, it is possible to calculate the intersection point information in the image.

$$ax + by + cz + d = 0 \qquad (8)$$

$$l = (x_0, y_0, z_0) + t(f, g, h) \qquad (9)$$

$$\left.\begin{array}{l}(x, y, z) = (x_0 + ft, y_0 + gt, z_0 + ht) \\ t = -(ax_0 + by_0 + cz_0 + d)/(af + bg + ch)\end{array}\right\} \qquad (10)$$

After that, on the display 25, the display controller 26d displays, in a formation of one or more rows, the candidates for the basic cross-sectional image, as well as the auxiliary cross-sectional images on each of which the information that was calculated at step S5 and indicates the positional relationships is superimposed (step S6). For example, the display controller 26d displays the auxiliary cross-sectional images that are each combined with the intersecting line information between the candidates for the basic cross-sectional image and the auxiliary cross-sectional image and the intersection point information with the long axis Y.

For example, as shown in FIG. 5, the display controller 26d displays each of the auxiliary cross-sectional images 200 and 201 combined with the intersecting line 100L with the first candidate 100 for the basic cross-sectional image and the intersecting line 101L with the second candidate 101, as well as the intersection point MV (e.g., marked with a square in FIG. 5) or the intersection point CA (e.g., marked with a triangle in FIG. 5) with the long axis Y.

Subsequently, the basic cross-sectional image generating unit 26b judges whether a generation instruction has been received from the operator indicating that an additional candidate for the basic cross-sectional image (hereinafter, an "additional candidate") should be generated (step S7). If such an instruction has been received (step S7: Yes), the basic cross-sectional image generating unit 26b calculates the position of the additional candidate and generates the additional candidate for the basic cross-sectional image from the volume data, according to the calculated position of the additional candidate (step S8).

After that, the display controller 26d further calculates relative positional relationships between the additional candidate and auxiliary cross-sectional images (step S5), displays the additional candidate for the basic cross-sectional image, and also displays, in each of the auxiliary cross-sectional images, information indicating the positional relationships between the additional candidate and the auxiliary cross-sectional image in a superimposed manner (step S6). The processes at steps S5 through S8 are repeatedly performed in this manner. On the contrary, if no generation instruction to generate an additional candidate is received from the operator, but an instruction to select a basic cross-sectional image is received, for example (step S7: No), the basic cross-sectional image generating unit 26b ends the process and sets the candidate selected by the operator as the basic cross-sectional image.

Possible embodiments are not limited to the processing procedure described above. For example, the candidates for the basic cross-sectional image and the auxiliary cross-sectional images may be displayed at the times when the cross-sectional images are generated. In other words, for example, the display controller 26d may display the candidates on the display 25 at the times when the candidates are generated by the basic cross-sectional image generating unit 26b at steps S2 and S3. Also, in another example, the display controller 26d may display the auxiliary cross-sectional images on the display 25 at the time when the auxiliary cross-sectional images are generated by the auxiliary cross-sectional image generating unit 26c at step S4.

Next, the generation of the additional candidate described above will be further explained, with reference to FIG. 5. By looking at the display 25, the operator is able to intuitively understand in what spatial directions the first candidate 100 and the second candidate 101 for the basic cross-sectional image are oriented, on the basis of the intersecting line 100L (e.g., the orientation of the short axis X) with the first candidate 100 for the basic cross-sectional image and the intersecting line 101L (e.g., the direction obtained by rotating the short axis X by the predetermined angle while the long axis Y is used as the rotation axis) with the second candidate 101 that are displayed in the auxiliary cross-sectional image 200.

Further, by looking at the display 25, the operator is also able to intuitively understand if the current position of the long axis Y goes through the center of the left ventricle LV, on the basis of the intersection point MV with the long axis Y displayed in the auxiliary cross-sectional image 200 and the intersection point CA with the long axis Y displayed in the auxiliary cross-sectional image 201.

According to medical knowledge, the short axis X of a four-chamber view such as the first candidate 100 for the basic cross-sectional image is usually oriented so as to go through a corner of the right ventricle RV and the long axis, in a left ventricular short-axis view near the basal part such as the auxiliary cross-sectional image 200. However, because there are individual differences in the shape of the heart among patients, it is necessary to fine-tune and check the position by rotating the short axis X while the long axis Y is used as the rotation axis. In this regard, according to the present embodiment, the operator is able to compare the images before and after fine-tuning the short axis X with each other, while the images are displayed in a row. Also, the operator is able to recognize in what spatial direction the short axis X is oriented in each situation, on the basis of the auxiliary cross-sectional images 200 and 201.

In the present embodiment, for example, the operator selects the second candidate 101 being displayed on the display 25 via the mouse included in the input unit 24 and inputs an instruction to set the second candidate 101 as the first candidate. Accordingly, the basic cross-sectional image generating unit 26b determines that a generation instruction has been received indicating that the second candidate 101 should be set as a new first candidate and that an additional candidate for the basic cross-sectional image should further be generated. In this situation, the additional candidate is, for example, a cross-sectional image obtained by further rotating the candidate 101 (i.e., the former second candidate) for the basic cross-sectional image by a predetermined angle. In other words, the basic cross-sectional image generating unit 26b rotates the short axis of the candidate 101 (i.e., the former second candidate) by the predetermined angle while the long axis Y is used as the rotation axis, so as to obtain a new short axis X. Further, the basic cross-sectional image generating unit 26b further rotates the candidate 101 (i.e., the former second candidate) by a predetermined angle while the long axis Y is used as the rotation axis, so as to obtain a new second candidate.

Figure 6:
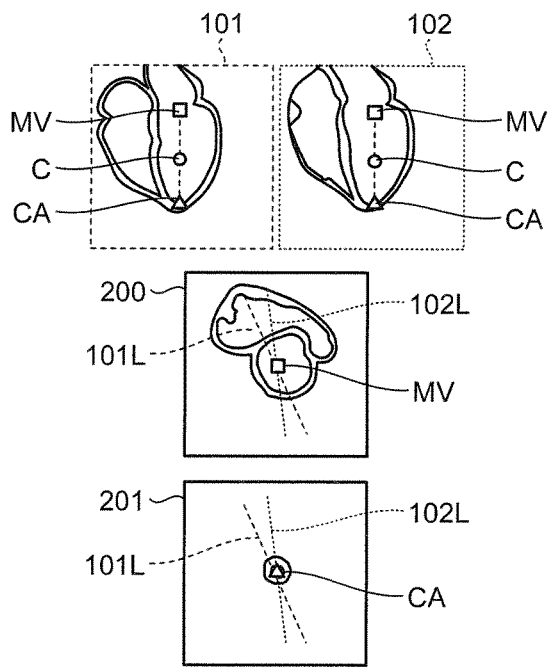
FIG. 6 is a drawing of an exemplary display of an additional candidate according to the present embodiment.

FIG. 6 is a drawing of an exemplary display of an additional candidate according to the present embodiment. For example, as shown in FIG. 6, the display controller 26d displays, as candidates for the basic cross-sectional image, the candidate 101 serving as the new first candidate and a candidate 102 serving as a new second candidate that are arranged in a row in a horizontal direction. Further, as shown in FIG. 6, below the candidates 101 and 102, the display controller 26d displays the auxiliary cross-sectional images 200 and 201 that are arranged in a row in a vertical direction. In this situation, for example, in each of the auxiliary cross-sectional images 200 and 201, the display controller 26d displays intersecting line information 102L that indicates a positional relationship between the new second candidate 102 and the corresponding one of the auxiliary cross-sectional images 200 and 201, in a superimposed manner.

Figure 7:
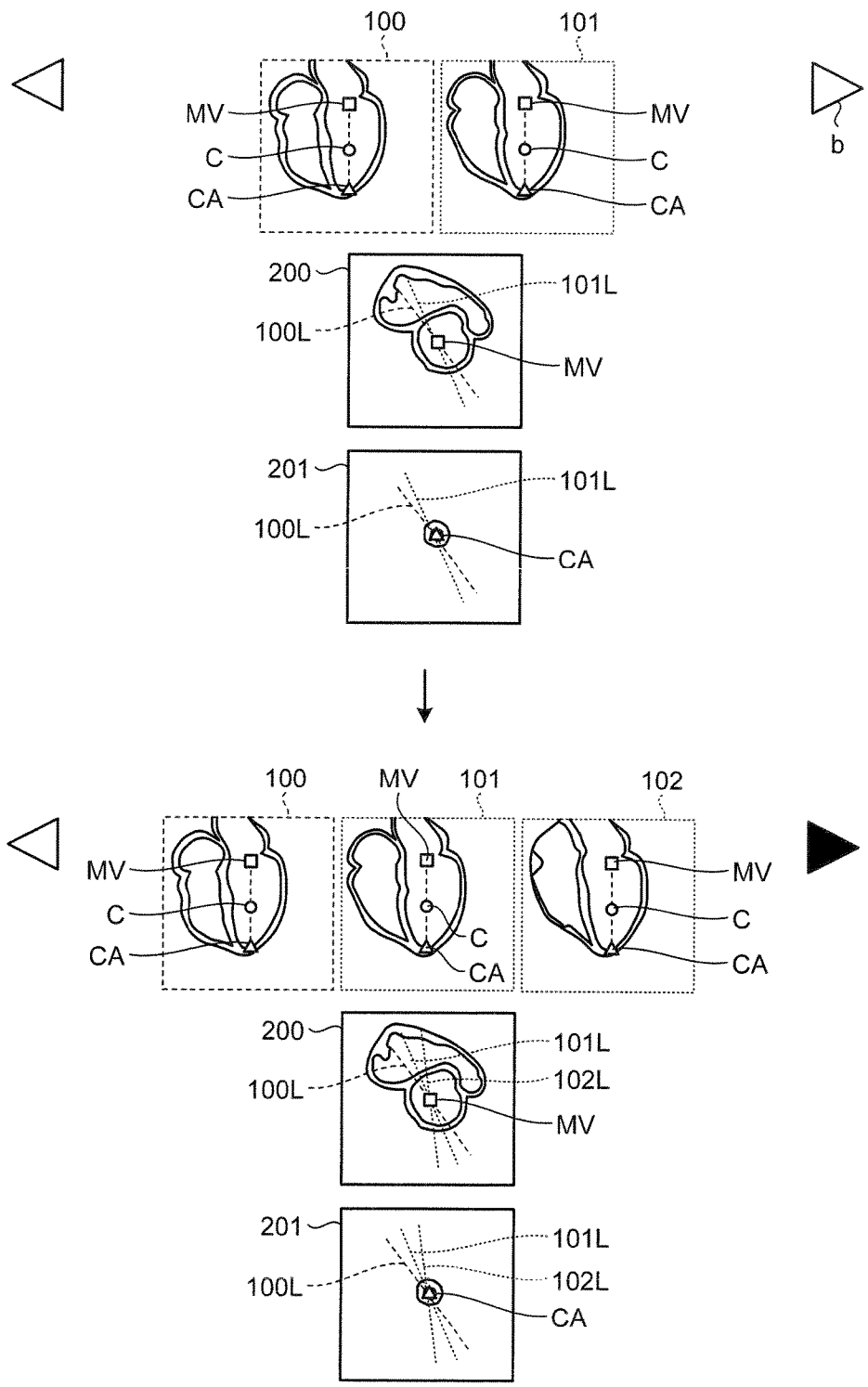
FIG. 7 is a drawing of another exemplary display of an additional candidate according to the present embodiment.

Possible embodiments are not limited to the examples described above. FIG. 7 is a drawing of another exemplary display of an additional candidate according to the present embodiment. For example, when displaying the cross-sectional images on the display 25, the display controller 26d may display therewith additional candidate generation instructing buttons "b" as shown in FIG. 7. In the example shown in FIG. 7, the additional candidate generation instructing buttons b indicate the rotation directions that can be used for generating an additional candidate by rotating one of the candidates while the long axis Y is used as the rotation axis. For example, if the operator has pressed the additional candidate generation instructing button b indicating the right direction, the basic cross-sectional image generating unit 26b determines that a generation instruction has been received indicating that a third candidate 102, which is an additional candidate for the basic cross-sectional image, should further be generated, separately from the first candidate 100 and the second candidate 101. In that situation, the third candidate 102 is, for example, a cross-sectional image obtained by further rotating the second candidate 101 by a predetermined angle. In other words, the basic cross-sectional image generating unit 26b uses the basic cross-sectional image obtained by further rotating the second candidate 101 by the predetermined angle while the long axis Y is used as the rotation axis, as the third candidate 102.

After that, for example, as shown in the lower half of FIG. 7, the display controller 26d displays, as candidates for the basic cross-sectional image, the third candidate 102 together with the first candidate 100 and the second candidate 101. The display controller 26d further displays, in each of the auxiliary cross-sectional images 200 and 201, the intersecting line information 102L indicating the positional relationship between the third candidate 102 and the corresponding one of the auxiliary cross-sectional images 200 and 201, in a superimposed manner.

The additional candidate generation instruction is not limited to the example described above. For example, by clicking a position between the first candidate 101 and the second candidate 102 while using the mouse included in the input unit 24, the operator may instruct that an additional candidate should be generated by rotating one of the candidates by an angle between the angles of the first candidate 101 and the second candidate 102 while the long axis Y is used as the rotation axis.

As another example, the operator may issue an instruction that an additional candidate should be generated, by inputting a change instruction to change the intersecting line information and/or the intersection point information that are displayed in the auxiliary cross-sectional images in a superimposed manner. In that situation, when having received a change instruction to change the intersecting line information and/or the intersection point information, the basic cross-sectional image generating unit 26b generates an additional candidate for the basic cross-sectional image, according to the received change instruction. For example, by using the mouse included in the input unit 24, the operator may move the intersection point MV or CA with the long axis Y that is displayed in one of the auxiliary cross-sectional images on the display 25. Accordingly, the basic cross-sectional image generating unit 26b changes the long axis Y, on the basis of the intersection point with the long axis Y that has been changed in the auxiliary cross-sectional image. For example, the basic cross-sectional image generating unit 26b may set a line segment that connects the intersection point with the long axis Y resulting from the change, to the other intersection point with the long axis Y that has not been changed, as a new long axis Y. Alternatively, the basic cross-sectional image generating unit 26b may translate the long axis Y (i.e., a parallel move), by an amount equal to the moving amount of the intersection point with the long axis Y due to the change. As a result of the change, the basic cross-sectional image generating unit 26b generates an additional candidate for the basic cross-sectional image. In yet another example, by using the mouse included in the input unit 24, the operator may change the orientation of the intersecting line information displayed in one of the auxiliary cross-sectional images. Accordingly, the basic cross-sectional image generating unit 26b generates an additional candidate for the basic cross-sectional image of which the angle resulting from the change corresponds to the orientation of the short axis X.

In yet another example, by using the keyboard included in the input unit 24, the operator may issue an instruction indicating that an additional candidate should be generated, by inputting the quantity of candidates for the basic cross-sectional image and/or a predetermined angle difference from the position of any of the candidates that are currently displayed on the display 25. In that situation, a basic cross-sectional image obtained by further rotating the second candidate 101 by the input angle while the long axis Y is used as the rotation axis is used as a third candidate 102.

With these arrangements described above, the operator is able to newly view the additional candidate for the basic cross-sectional image resulting from the change made through the input unit 24. After that, when the candidate selected by the operator is set as the basic cross-sectional image, the operator will be able to use the basic cross-sectional image in a diagnosis process.

As explained above, the MRI apparatus 100 according to the present embodiment arranges the one or more candidates obtained by rotating the basic cross-sectional image by the predetermined angle while the long axis is used as the rotation axis so as to be positioned along the horizontal (or the vertical) direction and also arranges, for example, the two or more second auxiliary cross sections each intersecting the long axis so as to be positioned along the vertical (or the horizontal) direction. Further, in each of the auxiliary cross-sectional images, the MRI apparatus 100 displays the intersection point with the long axis and the intersecting lines with the candidates for the basic cross-sectional image. With these arrangements, the user is able to efficiently recognize the positions of the basic cross-sectional images, the orientations of the long axes, and the cross-sectional images each obtained by rotating the short axis by the predetermined angle while the long axis is used as the rotation axis. As a result, according to the present embodiment, because the plurality of "candidates" for the basic cross-sectional image and the positional relationships between the "candidates" and the auxiliary cross-sectional images are displayed in the manner of a list, the operator is able to easily compare the plurality of candidates with one another in terms of the cross-sectional images themselves and the positional relationships between the short axis and the long axis, and is thus able to properly check the basic cross-sectional image.

Possible embodiments are not limited to the embodiment described above.

Figure 8:
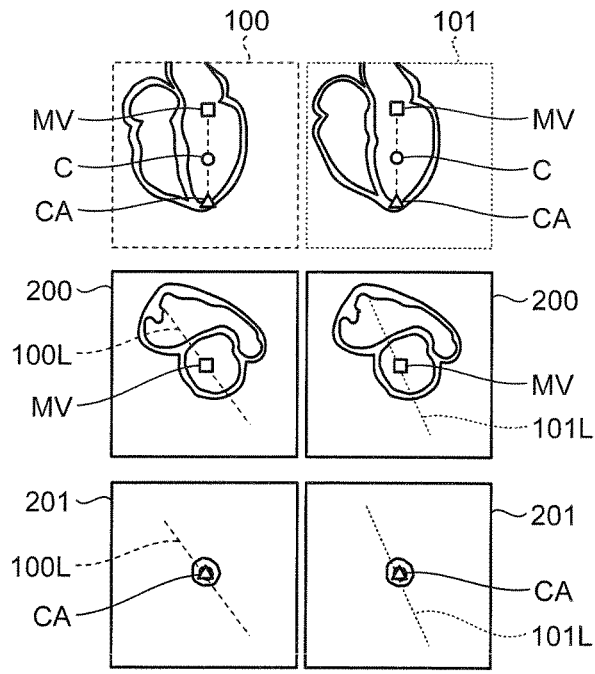
FIG. 8 is a drawing of an exemplary display according to another embodiment.

FIGS. 8 to 11 are drawings of exemplary displays according to other embodiments. In the embodiment described above, the example is explained in which, as illustrated in FIG. 5, the auxiliary cross-sectional images each of which is common to the candidates for the basic cross-sectional image are displayed, while the intersecting line information with respect to the plurality of candidates is displayed in each of the auxiliary cross-sectional images; however, possible embodiments are not limited to this example. For instance, it is also acceptable to display as many auxiliary cross-sectional images as the quantity of candidates. For example, as illustrated in FIG. 8, the display controller 26d may display the candidates for the basic cross-sectional image that are arranged in a row in the horizontal direction and may display the auxiliary cross-sectional images each of which corresponds to a different one of the candidates and which are arranged in a row in the vertical direction.

Figure 9:
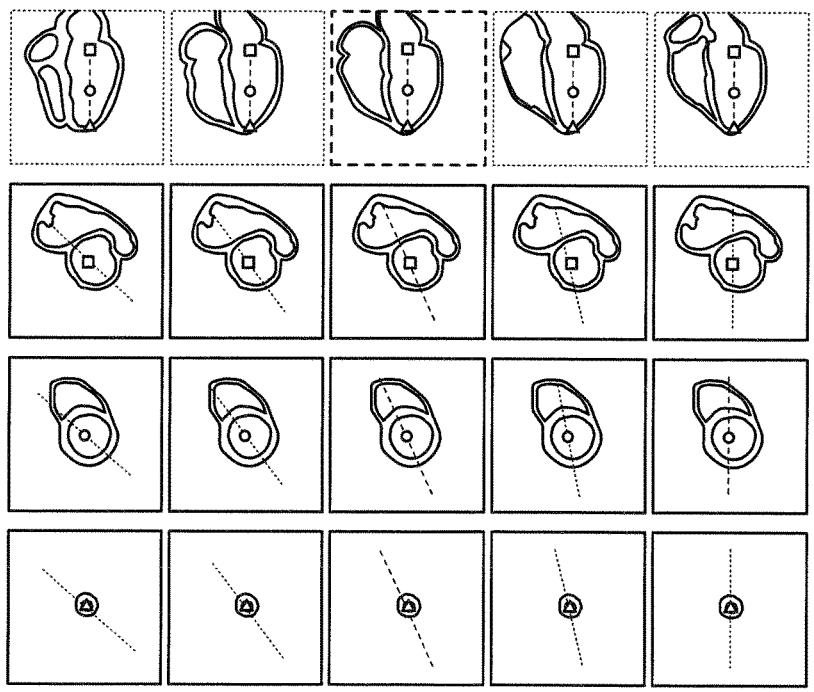
FIG. 9 is a drawing of an exemplary display according to yet another embodiment.

Further, in the embodiment described above, the example is explained in which, as illustrated in FIG. 5, the two candidates are displayed as the candidates for the basic cross-sectional image; however, possible embodiments are not limited to this example. It is acceptable to display three or more candidates. Further, in the embodiment described above, as illustrated in FIG. 5, the auxiliary cross-sectional images taken at the two locations are displayed; however, possible embodiments are not limited to this example. For instance, it is acceptable to display auxiliary cross-sectional images taken at three or more locations. For example, as illustrated in FIG. 9, the display controller 26d may display five candidates as the candidates for the basic cross-sectional image, for instance, and display auxiliary cross-sectional images taken at three locations.

Figure 10:
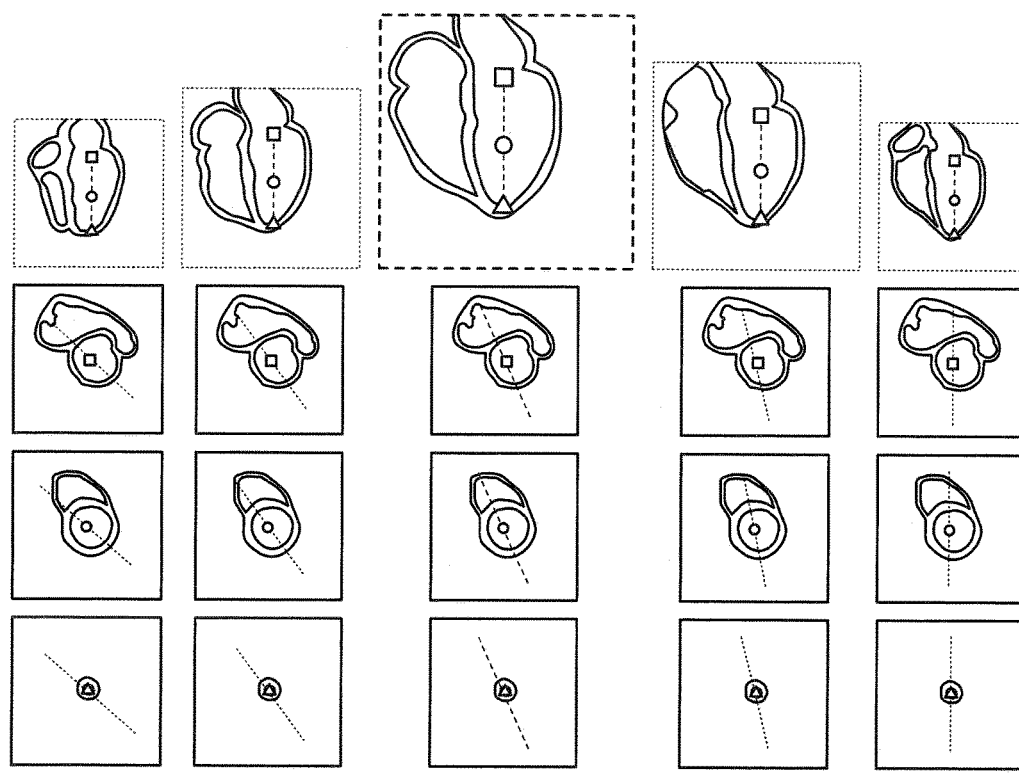
FIG. 10 is a drawing of an exemplary display according to yet another embodiment.

Further, the display controller 26d may vary the manner in which the candidates are displayed in accordance with the levels of probability of the candidates for the basic cross-sectional image. For example, it is more effective to configure the display controller 26d so as to, as illustrated in FIG. 10, vary the size of the images, on the basis of the levels of probability of the positions of the basic cross-sectional images calculated by the basic cross-sectional image generating unit 26b. In this situation, for example, the levels of probability of the positions of the basic cross-sectional images may be represented by matching errors based on a template matching process or may be represented by likelihood values output by a classifier that has been trained. For example, the basic cross-sectional image generating unit 26b may calculate the levels of probability as information expressed by numerical values. Alternatively, either instead of, or together with, varying the size of the images in accordance with the levels of probability, the display controller 26d may vary the type of a line used as the border of each image or the color in the background, for example. Alternatively, the display controller 26d may display the levels of probability expressed in numerical values within the images. In another example, either instead of, or together with, varying the size or the like of the basic cross-sectional images, the display controller 26d may vary the size or the like of the auxiliary cross-sectional images. With any of these arrangements, the operator is able to understand, at a glance, superiority and inferiority (i.e., the difference in the levels of probability) among the candidates for the basic cross-sectional image.

In yet another example, when generating the candidates for the basic cross-sectional image, the basic cross-sectional image generating unit 26b may adjust the quantity of candidates for the basic cross-sectional image or the angle by which any of the candidates is rotated while the long axis is used as the rotation axis, in accordance with the levels of probability of the candidates for the basic cross-sectional image. For example, when a first candidate for the basic cross-sectional image has been generated and if the level of probability of the first candidate exceeds a predetermined threshold value, the basic cross-sectional image generating unit 26b may decrease the quantity of candidates for the basic cross-sectional image, for example, or may reduce the angle by which the candidate is rotated while the long axis is used as the rotation axis, for example. The reason is that, if the level of probability of the first candidate is high, it is presumed that it is not necessary to have so many other candidates and that a proper basic cross-sectional image is not so different from the first candidate. On the contrary, if the level of probability of the first candidate for the basic cross-sectional image is lower than the predetermined threshold value, for example, the basic cross-sectional image generating unit 26b may increase the quantity of candidates for the basic cross-sectional image, for example, or may enlarge the angle by which the candidate is rotated while the long axis is used as the rotation axis, for example. The reason is that, if the level of probability of the first candidate is low, it is presumed that it is necessary to have other candidates in a certain quantity and that a proper basic cross-sectional image is different, to a certain extent, from the first candidate. The adjustments that can be made are not limited to these examples. It is acceptable to arbitrarily modify the adjustments according to the mode of operation.

Figure 11:
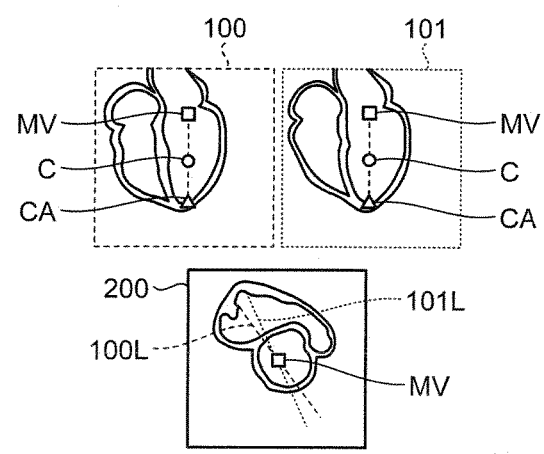
FIG. 11 is a drawing of an exemplary display according to yet another embodiment.

Further, in the embodiment described above, the auxiliary cross-sectional images taken in the two locations are displayed, as illustrated in FIG. 5; however, possible embodiments are not limited to this example. For instance, as illustrated in FIG. 11, it is also acceptable to display an auxiliary cross-sectional image taken only in one location.

Further, in the embodiment described above, the medical image diagnosis apparatus is assumed to be an MRI apparatus; however, possible embodiments are not limited to this example. For instance, the medical image diagnosis apparatus may be an X-ray diagnosis apparatus, an X-ray CT apparatus, or an ultrasound diagnosis apparatus. In another example, in place of the medical image diagnosis apparatus, an image display apparatus or an image processing system including a medical image diagnosis apparatus and an image display apparatus may execute the various types of processing processes described above. In this situation, the image display apparatus may be any of various apparatuses such as a workstation, an image storing apparatus (an image server) in a Picture Archiving and Communication System (PACS), an image viewer, or an electronic medical record system. For example, the image display apparatus may receive, from any of various types of medical image diagnosis apparatuses, an input of volume data that was acquired by the medical image diagnosis apparatus and is used as a processing target. In another example, the image display apparatus may receive an input of volume data stored in the image server of the PACS or the like and may use the received volume data as a processing target.

For example, the image display apparatus may include a display and a display controller. The display controller is configured to display, on the display, candidates for the basic cross-sectional image each of which contains the long axis of the heart and which are arranged in a row in either a horizontal direction or a vertical direction, as well as auxiliary cross-sectional images each of which intersects the candidates for the basic cross-sectional image and which display, in a superimposed manner, positional relationships with the candidates, while being arranged in a row in either the vertical direction or the horizontal direction that is different from the direction in which the candidates are arranged.

Figure 12:
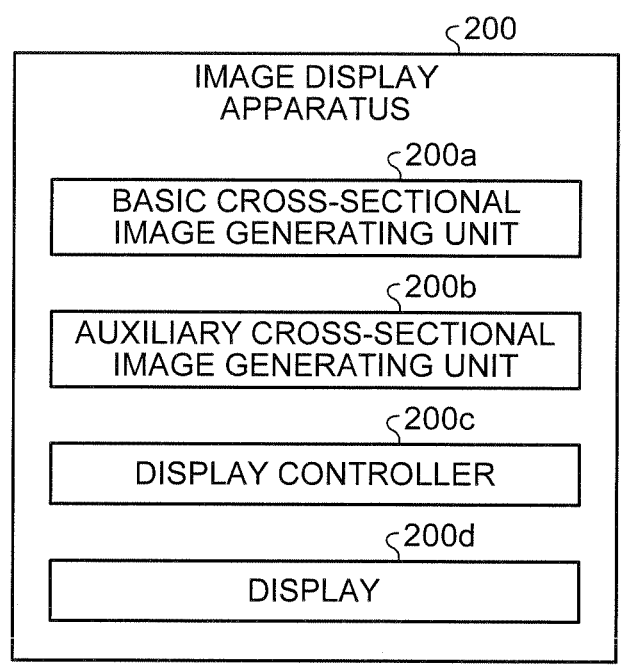
FIG. 12 is a block diagram of an image display apparatus according to yet another embodiment.

FIG. 12 is a block diagram of an image display apparatus according to yet another embodiment. For example, an image display apparatus 200 includes, as illustrated in FIG. 12, a basic cross-sectional image generating unit 200a, an auxiliary cross-sectional image generating unit 200b, a display controller 200c, and a display 200d. The basic cross-sectional image generating unit 200a, the auxiliary cross-sectional image generating unit 200b, the display controller 200c, and the display 200d have functions that correspond to those of the basic cross-sectional image generating unit 26b, the auxiliary cross-sectional image generating unit 26c, the display controller 26d, and the display 25 in the embodiment described above, respectively.

<The Basic Cross-Sectional Images Displayed as Position Determining Images>

The embodiment described above is not limited as to whether the basic cross-sectional images generated from the volume data are generated as images for determining the position of an image to be acquired in a main image taking process (i.e., an imaging scan) performed at the subsequent stage or are generated as images to be used in an analysis or diagnosis process. In this regard, an example in which the basic cross-sectional images are assumed to be generated as the position determining images will specifically be explained below.

Figure 13:
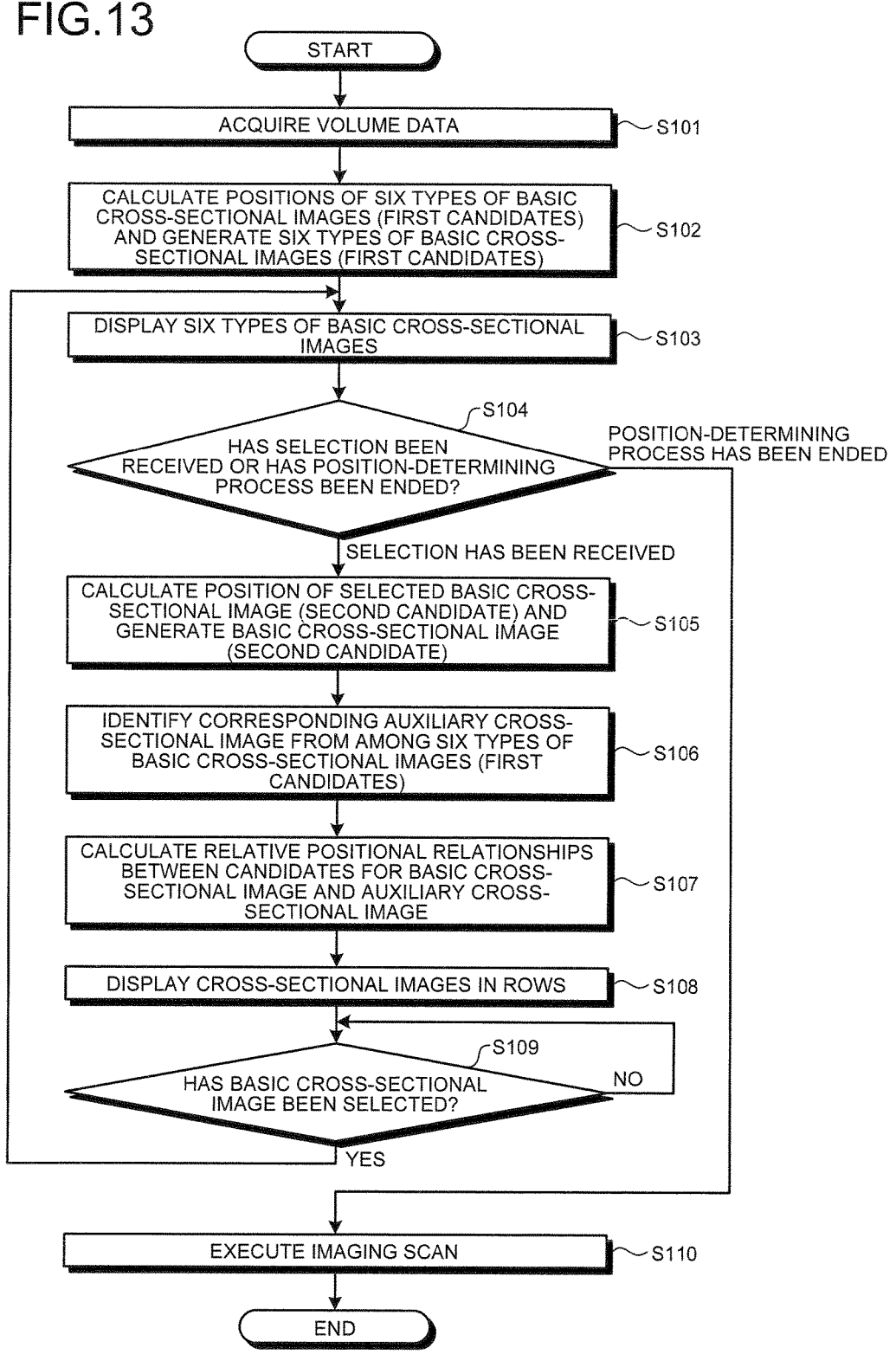
FIG. 13 is a flowchart of a processing procedure according to yet another embodiment.

FIG. 13 is a flowchart of a processing procedure according to yet another embodiment. First, the acquiring unit 26a performs an image taking process while using the heart of the patient P as a target site and acquires volume data of the heart (step S101). For example, the acquiring unit 26a acquires data of multi-slice images according to a predetermined image-taking region. Of the predetermined image-taking region, an image-taking region in a slice direction is, for example, a region defined by a position offset in the direction toward the head of the patient from the upper end of the heart and a position offset in the direction toward the feet of the patient from the lower end of the heart. Further, for example, the acquiring unit 26a acquires the data of the multi-slice images by using a two-dimensional (2D) Fast Field Echo (FFE), a 2D Steady-State Free Precession (SSFP), or a 2D Fast Asymmetric Spin Echo (FASE). The acquisition process is performed with a high level of resolution that allows cross-sectional images of the heart to be identifiable.

After that, the image reconstructing unit 22 generates volume data by reconstructing a plurality of axial cross-sectional images along the body axis direction of the patient P from the acquired data. For example, the volume data is represented by a group of twenty axial cross-sectional images reconstructed by the image reconstructing unit 22. The image reconstructing unit 22 may perform an isotropization process (i.e., an interpolating process performed while ensuring that the three directions of x-, y-, and z-directions are at intervals of equal distance) on the reconstructed volume data and may provide the process at the subsequent stage with the result serving as the volume data. Alternatively, the image reconstructing unit 22 may provide the process at the subsequent stage with the volume data on which no isotropization has been performed.

Subsequently, from the volume data acquired at step S101, the basic cross-sectional image generating unit 26b calculates positions of six types of basic cross-sectional images and generates the six-types of basic cross-sectional images from the volume data according to the calculated positions (step S102). The six types of cross-sectional images generated in this situation are generated as position-determining images for an image to be acquired during an imaging scan performed at the subsequent stage. In addition, in the sense that the six types of basic cross-sectional images are images prior to the operator's ending the position determining process, the six types of basic cross-sectional images are basic cross-sectional images corresponding to a first candidate. Further, as explained later, each of the basic cross-sectional images can serve as an auxiliary cross-sectional image for the other basic cross-sectional images.

Figure 14:
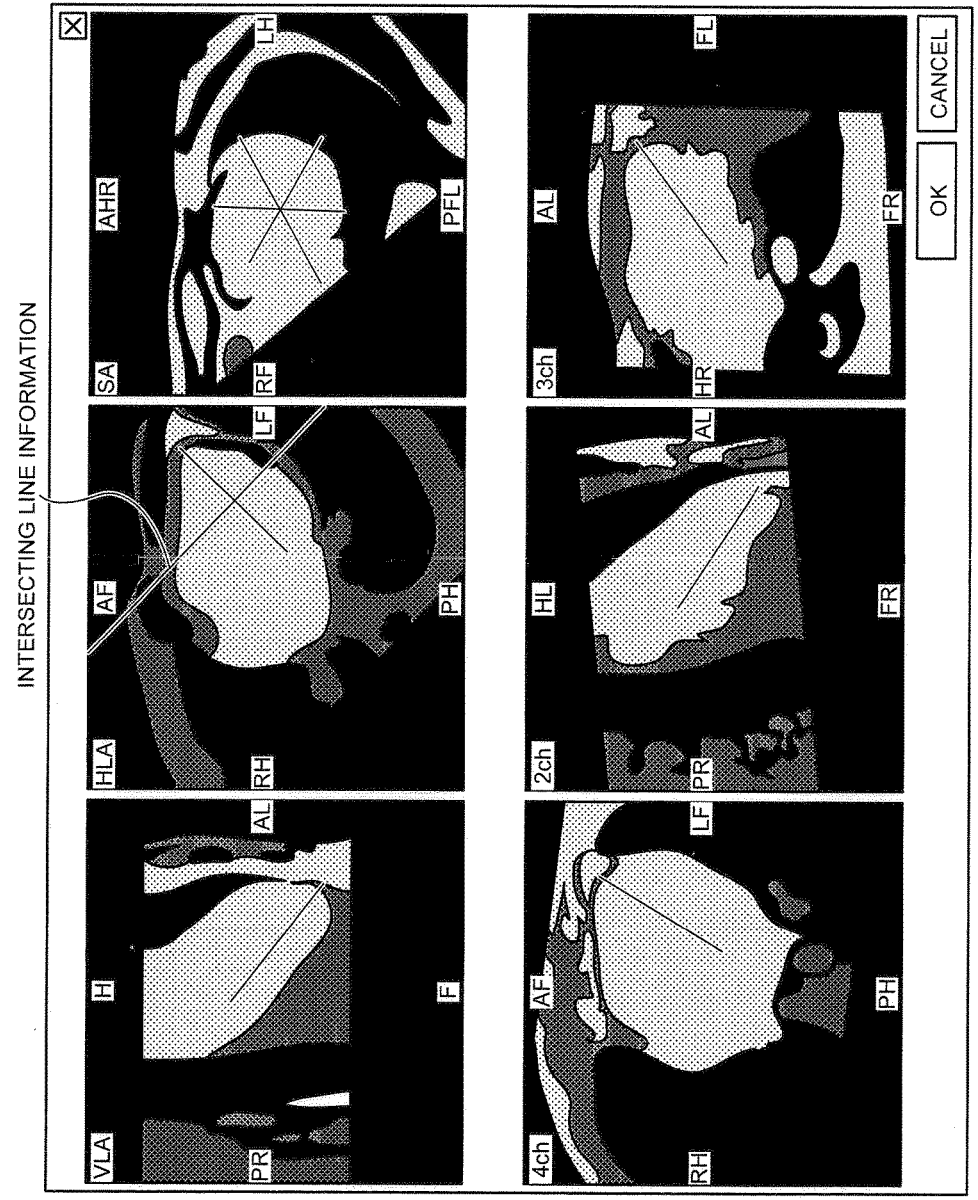
FIG. 14 is a drawing of an exemplary display of position determining images according to yet another embodiment.

After that, on the display 25, the basic cross-sectional image generating unit 26b displays the six types of cross-sectional images generated at step 3102 (step S103). FIG. 14 is a drawing of an exemplary display of the position determining images according to the other embodiment. For example, as illustrated in FIG. 14, the basic cross-sectional image generating unit 26b displays, as the position determining images, a vertical long-axis (VLA) view, a horizontal long-axis (HLA) view, a left ventricular short-axis (SA) view, a four-chamber (4ch) view, a two-chamber (2ch) view, and a three-chamber (3ch) view that are arranged in rows. As illustrated in FIG. 14, in each of the cross-sectional images, the basic cross-sectional image generating unit 26b may display intersecting line information with the other cross-sectional images, in a superimposed manner. Although omitted from FIG. 14 for the sake of convenience in the explanation, it is also acceptable to display the six types of cross-sectional images so as to be enclosed in borders in mutually-different colors, for example, so that it is possible to express which cross-sectional image the intersecting lines displayed in the cross-sectional images each correspond to, by matching the color of the border with the color of the intersecting line information.

Subsequently, the basic cross-sectional image generating unit 26b judges whether a selection on the basic cross-sectional image has been received or an instruction to end the position determining process has been received, from the operator, in the six types of basic cross-sectional images serving as the position determining images (step S104).

If a selection on the basic cross-sectional image has been received, the basic cross-sectional image generating unit 26b displays, after performing the processes at steps S105 through S107, candidates for the selected basic cross-sectional image and auxiliary cross-sectional images that are arranged in a matrix formation, in the same manner as described in the embodiment above (see FIG. 5, for example) and displays the arranged images on the display 25 (step S108). The images arranged in the matrix formation may be displayed in a window different from the window in which the six types of basic cross-sectional images are displayed at step S103. Alternatively, the images arranged in the matrix formation may be displayed next to the six types of basic cross-sectional images displayed at step S103, if all the images can fit on one screen, for example.

For instance, if a selection on the basic cross-sectional image has been received, the basic cross-sectional image generating unit 26b calculates the position of a second candidate for the selected basic cross-sectional image, in the same manner as described in the embodiment above and generates the second candidate for the basic cross-sectional image from the volume data, according to the calculated position of the second candidate (step S105).

Further, the auxiliary cross-sectional image generating unit 26c identifies an auxiliary cross-sectional image corresponding to the basic cross-sectional image selected at step S104 from among, for example, the six types of cross-sectional images generated at step S102 (step S106). For example, if the basic cross-sectional image selected by the operator at step S104 is the four-chamber view, the auxiliary cross-sectional image generating unit 26c identifies the left ventricular short-axis view, which is one of the basic cross-sectional images, as the corresponding auxiliary cross-sectional image.

In this situation, methods for identifying the auxiliary cross-sectional image include the following three examples. According to a first method, sets each made up of a basic cross-sectional image and an auxiliary cross-sectional image are prepared in advance. For example, as a result of inputs made by the operator in advance, the auxiliary cross-sectional image generating unit 26c may store therein, in advance, a set made up of the four-chamber view and the left ventricular short-axis view, as well as other sets. Further, if the basic cross-sectional image selected by the operator at step S104 is the four-chamber view, the auxiliary cross-sectional image generating unit 26c refers to the sets that are stored in advance and identifies the left ventricular short-axis view as the auxiliary cross-sectional image. As another example, the auxiliary cross-sectional image generating unit 26c may store therein, in advance, a set made up of "a long-axis view" and "a short-axis view" as a set in which the four-chamber view and the left ventricular short-axis view are expressed in a more abstract manner. For example, if the basic cross-sectional image selected by the operator at step S104 is the four-chamber view, which is a "long-axis view", the auxiliary cross-sectional image generating unit 26c may search for a "short-axis view" from among the six types of basic cross-sectional images and may identify the left ventricular short-axis view, which is a short-axis view, as the auxiliary cross-sectional image.

According to a second method, an auxiliary cross-sectional image is adaptively determined on the basis of relative positional relationships among the basic cross-sectional images. For example, with respect to the basic cross-sectional image selected by the operator at step S104, the auxiliary cross-sectional image generating unit 26c calculates relative positional relationships with the other basic cross-sectional images and identifies an auxiliary cross-sectional image by using whether the angle formed by two cross-sectional images is close to the right angle or not as a judgment criterion. According to a third method, a designation of an auxiliary cross-sectional image is received. For example, the auxiliary cross-sectional image generating unit 26c also receives a designation of an auxiliary cross-sectional image from the operator, like the basic cross-sectional image. The method for identifying the auxiliary cross-sectional image is not limited to these examples described above.

If necessary, in addition to the auxiliary cross-sectional image identified from among the basic cross-sectional images, the auxiliary cross-sectional image generating unit 26c may further generate, for example, another auxiliary cross-sectional image. For instance, if a left ventricular short-axis view that has already been generated as a basic cross-sectional image is a cross-sectional image in the position corresponding to the mitral valve MV, the auxiliary cross-sectional image generating unit 26c may generate another left ventricular short-axis view in the position corresponding to the cardiac apex CA as another auxiliary cross-sectional image.

Subsequently, in the same manner as in the embodiment described above, the display controller unit 26d calculates the relative positional relationships between the candidates for the basic cross-sectional image and the auxiliary cross-sectional image (step S107), and the process proceeds to the display procedure at step S108. Although omitted from FIG. 13, for example, in that situation also, if a generation instruction to generate an additional candidate for the basic cross-sectional image has been received from the operator, the basic cross-sectional image generating unit 26b may generate an additional candidate for the basic cross-sectional image from the volume data and may repeat the processes at steps S107 and S108 again. Further, in the basic cross-sectional images illustrated in FIG. 14, the intersecting line information with the other cross-sectional images is displayed in a superimposed manner; however, for example, in the display at step S108, the intersecting line information does not necessarily have to be displayed, because the intersecting line information is not necessary for the purpose of facilitating the checking performed by the operator.

After that, when having received a selection on the basic cross-sectional image from among a plurality of candidates for the basic cross-sectional image (step S109: Yes), the basic cross-sectional image generating unit 26b ends the basic cross-sectional image checking process and returns to the process of displaying six types of basic cross-sectional images on the display 25 again (step S103). In this situation, as for the basic cross-sectional image that has already been selected at step S104 from among the six types of basic cross-sectional images, the basic cross-sectional image selected by the operator at step S109 is displayed. Possible embodiments are not limited to the example in which the selection on one of the basic cross-sectional images is explicitly received. For example, receiving an operation of pressing a checking-process ending-button may replace the process of selecting the basic cross-sectional image, considering that pressing the button is equivalent to approving the basic cross-sectional image corresponding to the first candidate displayed at step S103.

On the contrary, when the basic cross-sectional image generating unit 26b has received an instruction to end the position determining process from the operator at step S104, the acquiring unit 26a then executes an imaging scan according to the position of the basic cross-sectional image confirmed as a result of the processes described above (step S110).

The procedure described above is merely an example. In the example above, the six types of basic cross-sectional images are generated from the volume data as the position determining images (see step S102), and the imaging scan is executed according to the position of the basic cross-sectional image confirmed at the preceding stage (see step S110). However, possible embodiments are not limited to this example. It is possible to arbitrarily modify the arrangements as to the quantity and the types of cross-sectional images that are at first generated from the volume data as the position determining images, as well as whether the cross-sectional images should be displayed in a list or individually. For example, it is sufficient if the basic cross-sectional image generating unit 26b generates two or more types of cross-sectional images. Further, it is also possible to arbitrarily modify the arrangement as to the quantity and the types of cross-sectional images that are acquired in the imaging scan. For example, it is sufficient if the acquiring unit 26a acquires one or more types of cross-sectional images.

Further, the quantity and the types of cross-sectional images generated as the position determining images are not necessarily dependent on the quantity and the types of cross-sectional images acquired in the imaging scan. For example, there may be a situation where a cross-sectional image that was not scheduled in the original plan is acquired due to a later change of plans. If the procedure needed to be started all over from the position determining process of the basic cross-sectional image every time a new cross-sectional image is acquired, the labor of the operator would increase accordingly. However, for example, with an arrangement in which the position determining process has been finished in advance for a larger number of types of cross-sectional images than the number of types of cross-sectional images scheduled in the imaging scan, it is possible to flexibly address such a change of plans.

The above explanation is based on the situation where the one example (e.g., the display illustrated in FIGS. 5 and 6) of the exemplary embodiments is applied; however, possible embodiments are not limited to this situation. The disclosure herein is similarly applicable to any of the modes of the exemplary embodiments described above. Further, in the description above, the example is explained in which the four-chamber view is selected as the basic cross-sectional image, while the corresponding auxiliary cross-sectional image is the left ventricular short-axis view. However, possible embodiments are not limited to this example. Any set made up of cross-sectional images that are in an intersecting relationship may be selected, as appropriate. In other words, for example, of the six types of basic cross-sectional images, any of the five types of basic cross-sectional images other than the basic cross-sectional image selected as the basic cross-sectional image that needs to be checked can serve as an auxiliary cross-sectional image. However, a desirable combination is one in which a long-axis view is selected as the basic cross-sectional image that requires the checking, whereas a short-axis view is selected as the corresponding auxiliary cross-sectional image. Further, in the situation where one of the basic cross-sectional images generated by the basic cross-sectional image generating unit 26b can serve as the auxiliary cross-sectional image as described above, the basic cross-sectional image generating unit 26b and the auxiliary cross-sectional image generating unit 26c may be configured as one processing unit.

<The Basic Cross-Sectional Images to be Displayed in the Process after the Imaging Scan>

The example has thus been explained on the assumption that the basic cross-sectional images generated from the volume data are generated and displayed as the position determining images for the image to be acquired in the imaging scan; however, possible embodiments are not limited to this example. For instance, the processes performed by the basic cross-sectional image generating unit 26b, the auxiliary cross-sectional image generating unit 26c, and the display controller 26d may be performed as post-processing processes on volume data acquired in the imaging scan. For example, the processes may be performed as a process for the purpose of finding a proper image to be used in an analysis or diagnosis process. Further, as described above, the medical image diagnosis apparatus does not necessarily have to be an MRI apparatus and may be an X-ray diagnosis apparatus, an X-ray CT apparatus, an ultrasound diagnosis apparatus, or the like. In this regard, for example, the processes described above may be performed for the purpose of checking or making adjustments on the generation of a Multi-Planar Reconstruction (MPR) image to be used in a diagnosis process, from volume data acquired by such a medical image diagnosis apparatus with a high level of resolution.

<The Order in which the Processes are Performed>

It is possible to arbitrarily modify the processing procedures (e.g., the flowcharts shown in FIGS. 4 and 13) explained in the embodiment above. For instance, in the embodiment described above, the example is explained in which the calculation of the positions of the cross-sectional images and the generation of the cross-sectional images are performed consecutively; however, possible embodiments are not limited to this example. It is possible to perform the cross-sectional image generating process itself, at any time before the images are displayed by the display controller 26d on the display 25. It should be noted, however, that it is also possible to utilize a previously-generated cross-sectional image in a process performed at a later stage. For example, at the stage when a basic cross-sectional image corresponding to a first candidate has been generated, the basic cross-sectional image generating unit 26b may determine the level of probability of the basic cross-sectional image corresponding to the first candidate and may adjust the quantity of candidates for the basic cross-sectional image and the angle by which the candidate is rotated while the long axis is used as the rotation axis, on the basis of the result of the determination.

Further, for example, it is also possible to change the order, as appropriate, as to whether the position of the second candidate for the basic cross-sectional image is calculated or the position of the auxiliary cross-sectional image is calculated, after the position of the first candidate for the basic cross-sectional image is calculated. As mentioned here, it is possible to arbitrarily modify the processing procedures explained in the exemplary embodiments above, except for those that are in dependency relationships such as the positions calculated in relation to the plurality of cross-sectional images serving as the candidates.

<Other Sites>

In the exemplary embodiments described above, the example is explained in which the "heart" is used as the target site; however, possible embodiments are not limited to this example. The disclosure herein is similarly applicable to situations where an image taking process is performed on other target sites. For example, the disclosure herein is similarly applicable to situations where an image taking process is performed on a joint such as a "shoulder" or a "knee". In that situation, on the display 25, the display controller 26d displays, in a formation of one or more rows, candidates for the basic cross-sectional image, as well as auxiliary cross-sectional images each displaying information indicating positional relationships with the basic cross-sectional image in a superimposed manner.

When an image taking process is performed on a shoulder joint, for example, a position determining process may be performed in an axial cross-sectional image, for an imaging scan of an oblique coronal cross-sectional image positioned parallel to the scapula or an oblique sagittal cross-sectional image positioned orthogonal to the scapula. In that situation, for example, the basic cross-sectional image generating unit 26b generates and displays a first candidate for the oblique coronal cross-sectional image or the oblique sagittal cross-sectional image serving as the basic cross-sectional image, from volume data acquired with a relatively low level of resolution for a position-determining purpose. Further, for example, when having received a selection on the basic cross-sectional image from the operator, the basic cross-sectional image generating unit 26b generates a second candidate for the selected basic cross-sectional image. The auxiliary cross-sectional image generating unit 26c, on the other hand, generates, from the volume data, the axial cross-sectional image as an auxiliary cross-sectional image corresponding to the selected basic cross-sectional image. Further, on the display 25, the display controller 26d displays, in a formation of one or more rows, the first and the second candidates for the basic cross-sectional image (e.g., the oblique coronal cross-sectional image) as well as the auxiliary cross-sectional image (e.g., the axial cross-sectional image) displaying the information indicating the positional relationships with the basic cross-sectional images in a superimposed manner.

<The Cross-Sectional Images and the Directions>

In the exemplary embodiments described above, the example is explained in which the various types of cross-sectional images generated from the volume data are referred to as a "basic cross-sectional image" and "auxiliary cross-sectional images" depending on the purpose thereof as appropriate, so that the display controller displays the candidates for the "basic cross-sectional image" and the "auxiliary cross-sectional images"; however, possible embodiments are not limited to this example. These cross-sectional images do not necessarily have to be of types such as the "basic cross-sectional image" and the "auxiliary cross-sectional images". In other words, it is sufficient if the medical image diagnosis apparatus or the image display apparatus simply generates and/or displays cross-sectional images (i.e., a first cross-sectional image and a second cross-sectional image that intersects the first cross-sectional image) from the volume data. Further, in the exemplary embodiments described above, the example is explained in which the candidates for the basic cross-sectional image are arranged in the horizontal (or the vertical) direction, whereas the auxiliary cross-sectional images are arranged in the vertical (or the horizontal) direction. In this situation, the "horizontal direction" and the "vertical direction" are directions that are substantially parallel to two sides of the display having a rectangular shape, for example. However, possible embodiments are not limited to this example. It is sufficient if the candidates for the basic cross-sectional image and the auxiliary cross-sectional images are arranged in a first direction and a second direction that intersects the first direction. Further, typically, the second direction is perpendicular to the first direction.

When the medical image diagnosis apparatus and the image display apparatus according to at least one aspect of the exemplary embodiments described above are used, it is possible to check the cross-sectional images properly.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus configured to assist an operator in choosing from plural cross-sectional images one that satisfies a predetermined condition based on review of an intersecting cross-sectional image, said apparatus comprising:
   digital signal processing circuitry and a display screen that are configured to
   calculate positions of a plurality of candidate images which are to be candidates for a first cross-sectional image from three-dimensional image data obtained by taking images of a heart,
   generate the candidate images from the three-dimensional image data according to the calculated positions of the candidate images,
   generate, from the three-dimensional image data, one or more second cross-sectional images each of which intersects the candidate images, and
   display in parallel on said display screen, the candidate images, as well as the second cross-sectional images on each of which information is superimposed, wherein the superimposed information indicates positional relationships between the candidate images and the second cross-sectional image,
   wherein the digital signal processing circuitry is configured to vary a manner in which the candidate images are displayed, in accordance with levels of probability that the positions of the candidate images satisfy said predetermined condition.

2. The medical image diagnosis apparatus according to claim 1, wherein the digital signal processing circuitry and display screen are configured to display the candidate images that are arranged in a row in a first direction and to display the second cross-sectional images that are arranged in a row in a second direction that intersects the first direction.

3. The medical image diagnosis apparatus according to claim 2, wherein the second direction is perpendicular to the first direction.

4. The medical image diagnosis apparatus according to claim 1, wherein the digital signal processing circuitry is configured to generate a first candidate image for the first cross-sectional image that is a cross-sectional image containing the long axis of the heart and a second candidate image for the first cross-sectional image that is a cross-sectional image obtained by rotating the position for the second candidate image from that used for the first candidate image by a predetermined angle while the long axis is used as a rotation axis.

5. The medical image diagnosis apparatus according to claim 1, wherein the digital signal processing circuitry is configured to generate at least one of said second cross-sectional images orthogonal to the long axis of the heart and in positions containing at least one of a mitral valve and a cardiac apex.

6. The medical image diagnosis apparatus according to claim 1, wherein, in each of the second cross-sectional images, the digital signal processing circuitry and display screen are configured to display at least one of the following in a superimposed manner: intersecting line information about intersecting lines between the candidate images and the second cross-sectional image; and intersection point information about intersection points between long axes contained in the candidate images and the second cross-sectional image.

7. The medical image diagnosis apparatus according to claim 1, wherein
the digital signal processing circuitry is configured to generate an additional candidate image for the first cross-sectional image according to an input from an operator, and
when the additional candidate image has been generated, the digital signal processing circuitry and display screen are configured to display the additional candidate image either together with, or instead of, the candidate images and to further display, in each of the second cross-sectional images, information indicating a positional relationship between the additional candidate image and the second cross-sectional image, in a superimposed manner.

8. The medical image diagnosis apparatus according to claim 7, wherein
the digital signal processing circuitry is configured to receive, as the input from the operator, a generation instruction to generate either a cross-sectional image rotated by an angle between angles of two of the candidate images or a cross-sectional image obtained by further rotating any of the candidate images by a predetermined angle, and
the digital signal processing circuitry is further configured to generate the additional candidate image for the first cross-sectional image according to the received generation instruction.

9. The medical image diagnosis apparatus according to claim 7, wherein
the digital signal processing circuitry is configured to receive, as the input from the operator, a change instruction to change at least one candidate image position based on at least one of intersecting line information and intersection point information that are displayed in the second cross-sectional images in a superimposed manner, and
the digital signal processing circuitry is further configured to generate the additional candidate image for the first cross-sectional image according to the received change instruction.

10. The medical image diagnosis apparatus according to claim 7, wherein
the digital signal processing circuitry is configured to receive, as the input from the operator, at least one of the following: a quantity of the candidate images; and an angle by which any of the candidate images is rotated while the long axis is used as a rotation axis, and
the digital signal processing circuitry is further configured to generate the additional candidate image for the first cross-sectional image according to specifics of the received input.

11. The medical image diagnosis apparatus according to claim 7, wherein
the digital signal processing circuitry is configured to receive, as an input from the operator, at least one of the following: a quantity of second cross-sectional images to be displayed; and positions of the second cross-sectional images, and
the digital signal processing circuitry is further configured to generate the second cross-sectional images according to the received input.

12. The medical image diagnosis apparatus according to claim 1 wherein the digital signal processing circuitry is configured to vary at least one of the following in accordance with the levels of probability that the positions of the candidate images satisfy said predetermined condition: sizes of the cross-sectional images; types of lines used as borders of the cross-sectional images; and background colors.

13. The medical image diagnosis apparatus according to claim 1, wherein the digital signal processing circuitry is configured to adjust at least one of the following, in accordance with the levels of probability that the positions of the candidate images satisfy said predetermined condition: a quantity of the candidate images to be displayed; and an angle by which any of the candidate images is rotated while the long axis is used as a rotation axis.

14. The medical image diagnosis apparatus according to claim 1, wherein the digital signal processing circuitry is configured to generate a plurality of types of first cross-sectional images as position-determining-purpose images from the three-dimensional image data acquired for a purpose of determining a position of a main image taking process and identify a first candidate image for the first cross-sectional images and the second cross-sectional image corresponding to the first candidate image from among the plurality of types of first cross-sectional images.

15. The medical image diagnosis apparatus according to claim 14, wherein, the digital signal processing circuitry is configured to identify, from among the plurality of types of first cross-sectional images, a first cross-sectional image containing a long axis of the heart as the first candidate image and identifies a first cross-sectional image containing a short axis of the heart as the second cross-sectional image.

16. The medical image diagnosis apparatus according to claim 1, wherein the information indicating the positional relationships includes intersection point information about intersection points between long axes contained in the candidate images and the second cross-sectional image.

17. The medical image diagnosis apparatus according to claim 16, wherein the digital signal processing circuitry and the display screen are further configured to display, in each of the candidate images in a superimposed manner, the intersection point information about intersection points.

18. A medical image diagnosis apparatus configured to assist an operator in choosing from plural cross-sectional images one that satisfies a predetermined condition based on review of an intersecting cross-section image, said apparatus comprising:
digital signal processing circuitry and a display screen that are configured to
calculate positions of a plurality of candidate images which are to be candidates for a first cross-sectional image from three-dimensional image data obtained by taking images of a predetermined site,
generate the candidate images from the three-dimensional image data according to the calculated positions of the candidate images,
generate, from the three-dimensional image data, one or more second cross-sectional images each of which intersects the candidate images, and
display in parallel on the display screen, the candidate images, as well as the second cross-sectional images on each of which information is superimposed, wherein the superimposed information indicates positional relationships between the candidate images and the second cross-sectional image,
wherein the digital signal processing circuitry is configured to vary a manner in which the candidate images are displayed, in accordance with levels of probability that the positions of the candidate images satisfy said predetermined condition.

19. An image display apparatus configured to assist an operator in choosing from plural cross-sectional images one that satisfies a predetermined condition based on review of an intersecting cross-sectional image, said apparatus comprising:

a display screen; and a digital signal processing circuitry configured to display, on the display screen, candidate images which are to be candidates for a first cross-sectional image each of which contains a long axis of a heart and which are arranged in a row in a first direction and to display, on the display screen, one or more second cross-sectional images each of which intersects the candidate images and which display, in a superimposed manner, information indicating positional relationships with the candidate images while being arranged in a row in a second direction that intersects the first direction, wherein the digital signal processing circuitry is configured to vary a manner in which the candidate images are displayed in accordance with levels of probability that positions of the candidate images calculated from three-dimensional image data obtained by taking images of the heart satisfies said predetermined condition.

* * * * *